United States Patent
Burge et al.

(10) Patent No.: US 12,053,240 B2
(45) Date of Patent: Aug. 6, 2024

(54) SYSTEMS AND METHODS FOR MEASUREMENT OF OPTICAL WAVEFRONTS

(71) Applicant: ARIZONA OPTICAL METROLOGY LLC, Tucson, AZ (US)

(72) Inventors: James Burge, Tucson, AZ (US); Chunyu Zhao, Tucson, AZ (US)

(73) Assignee: ARIZONA OPTICAL METROLOGY LLC, Tucson, AZ (US)

( * ) Notice: Subject to any disclaimer, the term of this patent is extended or adjusted under 35 U.S.C. 154(b) by 491 days.

(21) Appl. No.: 17/323,231

(22) Filed: May 18, 2021

(65) Prior Publication Data
US 2021/0361159 A1     Nov. 25, 2021

Related U.S. Application Data

(60) Provisional application No. 63/027,881, filed on May 20, 2020.

(51) Int. Cl.
| | | |
|---|---|---|
| *A61B 3/10* | (2006.01) | |
| *A61B 3/15* | (2006.01) | |
| *G01B 9/021* | (2006.01) | |

(52) U.S. Cl.
CPC ............ *A61B 3/1015* (2013.01); *A61B 3/152* (2013.01); *G01B 9/021* (2013.01)

(58) Field of Classification Search
CPC ...... A61B 3/1015; A61B 3/152; G01B 9/021; G01B 9/02068; G01B 11/272; G01B 9/02039; G01M 11/0271; G01M 11/005
See application file for complete search history.

(56) References Cited

U.S. PATENT DOCUMENTS

| | | | |
|---|---|---|---|
| 5,530,547 A | 6/1996 | Arnold | |
| 5,546,186 A | 8/1996 | Ohi | |
| 5,808,724 A | 9/1998 | Ina et al. | |
| 6,100,979 A | 8/2000 | Drabarek et al. | |

(Continued)

OTHER PUBLICATIONS

Beier, Matthias et al., "Development, fabrication, and testing of an anamorphic imaging snap-together freeform telescope," Applied Optics, vol. 54, No. 12, Apr. 20, 2015, 13 pages, http://dx.doi.org/10.1364/AO.54.003530.

(Continued)

*Primary Examiner* — James C. Jones
(74) *Attorney, Agent, or Firm* — Paradice & Li LLP

(57) ABSTRACT

An analytic tool for supporting alignment of an optical component in preparation for an interferometric test and performance of such a test. Apparatus and methods involve employment of the datum features on the optical component and/or metrology frame supporting such component. The metrology frame may include a secondary set of holograms (provided for use with a conventional system already employing a primary hologram that forms the testing optical wavefront). The conventional primary hologram is preferably substituted with a set of primary holograms (contained in the same, unitary or spatially-complementary housing sets) that perform different but complementary functions and that facilitate the alignment of the metrology frame with or without the tested optical component.

25 Claims, 10 Drawing Sheets

(56) References Cited

U.S. PATENT DOCUMENTS

| | | | |
|---|---|---|---|
| 7,072,042 | B2 | 7/2006 | Kim et al. |
| 7,605,926 | B1 | 10/2009 | Hetzler et al. |
| 7,643,149 | B2 | 1/2010 | Freimann et al. |
| 7,808,646 | B2 | 10/2010 | Rembe et al. |
| 7,848,031 | B2 | 12/2010 | Hetzler et al. |
| 9,234,741 | B2 | 1/2016 | Liang et al. |
| 9,651,358 | B2 | 5/2017 | Cobb et al. |
| 10,502,545 | B2 | 12/2019 | Wegmann et al. |
| 2015/0036149 | A1 | 2/2015 | Fouraz |
| 2018/0106591 | A1 | 4/2018 | Hetzler et al. |
| 2019/0250392 | A1 | 8/2019 | Cuche et al. |
| 2020/0225028 | A1 | 7/2020 | Hetzler et al. |
| 2020/0225029 | A1* | 7/2020 | Riepenhausen .... G01M 11/0271 |

OTHER PUBLICATIONS

Beier, Matthias et al., "Measuring position and figure deviation of freeform mirrors with computer generated holograms," Imaging and Applied Optics, Jan. 2015, 3 pages, https://opg.optica.org/abstract.cfm?URI=Freeform-2015-FT3B.2.

Burge, Jim, et al., "Optical test alignment using computer generated holograms," OSA/OFT Jun. 2002, 3 pages, https://opg.optica.org/abstract.cfm?uri=OFT-2002-OWD2.

Burge, James, et al., "Optical alignment with computer generated holograms," Proc. SPIE 6676, Sep. 21, 2007, 12 pages, doi: 10.1117/12.735853.

Hartung, Johannes, et al., "Measurement and correction of two-sided freeform optical elements with combined tactile-optical metrology equipment," EPJ Web of Conferences 2019, 2 pages, https://doi.org/10.1051/epjconf/201921508002.

Parks, Robert E., "Computer Generated Holograms as Fixtures for Testing Optical Elements," IODC, Freeform, OFT, Jul. 2017, 3 pages, https://doi.org/10.1364/FREEFORM.2017.JTh4B.4.

Parks, Robert, "Optical Alignment using a CGH and an autostigmatic microscope," Proc. SPIE 10377, Aug. 22, 2017, 13 pages, doi: 10.1117/12.2273033.

Song, Jae-Bong et al., "Modified alignment CGHs for aspheric surface test," Proc. SPIE 7426, Aug. 21, 2009, 9 pages, doi: 10.1117/12.826659.

* cited by examiner

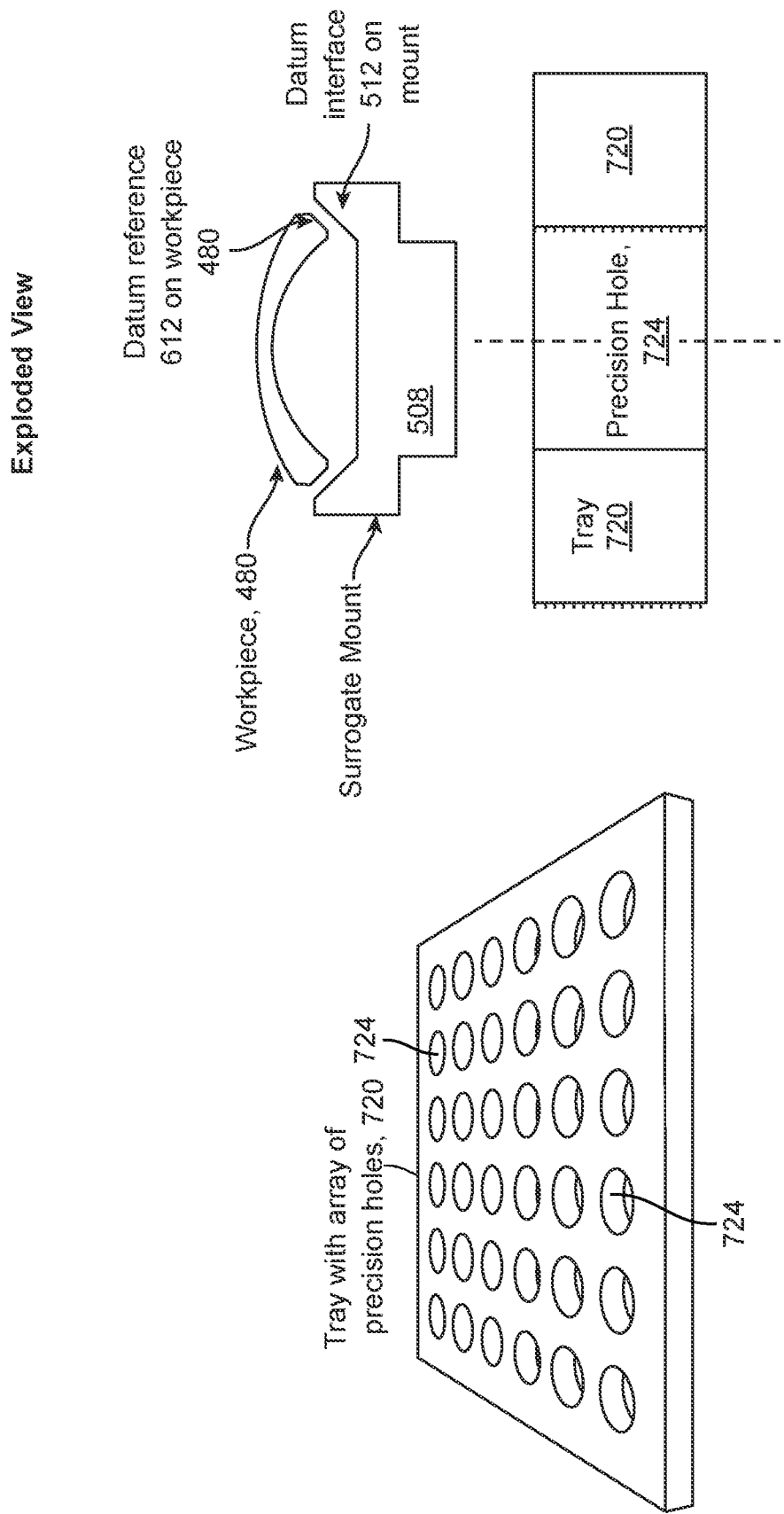

SYSTEMS AND METHODS FOR MEASUREMENT OF OPTICAL WAVEFRONTS

CROSS-REFERENCE TO RELATED APPLICATIONS

This US Patent application claims priority from and benefit of the U.S. Provisional Patent Application No. 63/027,881 filed on May 20, 2020, the disclosure of which is incorporated herein by reference.

TECHNICAL FIELD

This invention relates generally to optical metrology and, in particular, to optical measurements of aspheric optical wavefronts (for example, those representing and/or associated with optical components and systems having aspheric surfaces) with the use of optical interferometry.

RELATED ART

The use of wavefront sensing (in particular—optical interferometry and, specifically, phase-shifting interferometry) with computer-generated hologram-based correction is recognized as a standard method for measuring aspheric surfaces.

Phase-shift interferometry is an established method for measuring a variety of physical parameters that range from the shape of optical components to the density of gas in aerodynamic flow fields. An interferometric wavefront sensor, which employs phase-shift interferometry, typically includes a temporally-coherent light source (such as a laser, for example), the light output from which is spatially split to define two optical wavefronts (a reference optical wavefront and a test or object optical wavefront) propagating along different optical paths and later recombined after traversing different path lengths. Upon the recombination, the relative phase difference between these two wavefronts manifests as a two-dimensional intensity pattern known as an interferogram. Phase-shift interferometers typically have an element in the path of the reference wavefront that is configured to introduce multiple (usually three or more) known phase-steps or phase-shifts into the reference wavefront. By acquiring, with an optical detector, the irradiance patterns or interferograms corresponding to each of such phase-shifts, the phase distribution of the object wavefront can be quantitatively and rapidly calculated independently from the irradiance in the reference wavefront or the object wavefront.

An example 100, illustrating the process of testing of the workpiece 136 with the use of the optical measurement system 140 (containing the commercially-available phase-shifting interferometric system 110 that is judiciously equipped for testing optical components) is schematically illustrated in FIG. 1. Here, the optical system of the interferometer 110 (shown in this example as a Fizeau interferometer) spatially expands a light output from a laser source (not shown) to a collimated beam of light (not shown) and delivers it to the Fizeau transmission sphere 114. The interchangeable (replaceable) Fizeau transmission sphere 114 changes or modifies the degree of collimation of this beam of light as desired, and converges the substantially-spherical optical wavefront 118 towards the focal point 120. Upon passing the focal point 120, the spherical wavefront starts spatially expanding to form the wavefront 124. At the same time, the transmission sphere 114 partially reflects (not shown) a portion of the collimated beam incident onto the sphere 114 back to the interferometer 110, to form a reference wavefront that is used in the interferometric measurement.

The object optical wavefront 124 from the interferometer is transformed by the holographic component or system 128 (often—the one containing a computer-generated hologram, or CGH, as shown) to the testing wavefront 132 that closely (or substantially) matches the spatial profile of the surface 136A of an optical component under test (or, interchangeably, a workpiece under test or unit under test, UUT) 136. The light reflected from or by this surface 136A (indicated with the double-headed arrow 140) propagates back through the CGH 128 into the interferometer 110, where it is combined with the reference wavefront (formed by light reflected into the interferometer by the reference surface). Fringes of interference (interferometric fringes, interferograms) formed as a result of such optical interference are imaged onto an optoelectronic sensor or optical detector of the measurement system 140 (not shown). The phase of light in the measurement system 140 is discretely shifted as the sequence of discrete images are acquired at the optical detector. This sequence of images is used to determine the shape (or spatial profile) difference between the two interferometrically-combined wavefronts (the reference wavefront and the wavefront formed by light from the testing wavefront 132 that has been reflected by the surface 136A). By carefully controlling and calibrating the reference wavefront, the shape departure from the ideal (or desired, or targeted) shape for the surface 136A under test can then be determined as known in related art.

Often, a CGH 128 is manufactured onto (in cooperation with) a flat glass substrate or optical plate, which is mounted into a dedicated kinematic fixture 200 that includes a metallic frame 204 (see example of FIG. 2). The fixture 200 is typically equipped with steel spheres or balls such that the spatial position of the holographic pattern of the component 128 is tightly controlled with respect to the steel balls. Such mounting facilitates interchangeability of CGH 128 using kinematic seats to define the positions of the balls. A dedicated standard alignment CGH 128 can be used for optical alignment. Once the alignment is complete, this alignment CGH may be removed from the kinematic fixture 200, and replaced with a different CGH, while the accuracy of the positioning of the new holographic pattern with respect to the balls is maintained within the acceptable window or range of deviation.

The challenges and recognized limitations of this currently-accepted and used in related art methodology of measurement manifest in how precisely the target aspheric surface of a given workpiece under test can be spatially positioned with respect to the testing (measurement) wavefront 132. The precision of such positioning, as will be readily understood by a skilled artisan, directly affects the spatial profile of the measurement wavefront 132 at the moment of incidence onto the workpiece or the unit under test (UUT). (For example, optical wavefronts that are spatially expending will have a radius of curvature that increases as the wavefront propagates, so if the surface under test 136A—in the example of FIG. 1—is positioned too far away from the generator of the testing wavefront 132—here, the CGH 128—the wavefront 132 will have a larger radius of curvature at the moment of incidence on the surface 136A. A workpiece 136 that ensures a null measurement in this situation will necessarily have a radius of curvature of the surface 136A that is too large for practical use. This situation persists for aspherical as well as spherical wavefronts.) The challenges originate from the adoption of a variety of rather complex aspheric surfaces that are now required in production of optical systems that must achieve very high quality of optical imaging. Additional degrees of freedom beyond the spacing must be controlled in the test configuration for the accurate measurement of aspheric surfaces.

As a person of skill in the art will readily appreciate, the simplest aspheric surfaces are shapes defined by conic sections of revolution, such as paraboloid, ellipsoid, and hyperboloid. For increased performance in the optical system, additional polynomial terms are often added to the function of revolution. Often, an optical system will use only an off-axis portion of such an axisymmetric shape such that it is impractical to make or measure the full parent. A general class of aspheric surfaces are now being used that are called "freeform surfaces," which can include nearly any smooth shape defined by numerical functions or even defined as grids of points. While some methods of controlling the configuration of the test system such as the system 100 have been implemented, there remains an unsatisfied need in solutions for quick and precise alignment of the UUTs with aspherical surfaces that lend themselves to measurement en masse, with high throughput.

SUMMARY

Embodiments of the invention provide an apparatus for measuring an optical wavefront representing an optical workpiece under test, that facilitates the alignment of the workpiece with respect to all six degrees of freedom. Such apparatus includes a wavefront sensor and first and second repositionable systems located across the axis of the apparatus and one after another with respect to an output from the wavefront sensor. The first repositionable system contain a first alignment hologram, a first measurement hologram, and a second alignment hologram such as to form a primary alignment wavefront (by reflecting a first portion of the light output from an optical wavefront delivered from the wavefront sensor and incident onto the first repositionable optical system) and to transmit a second portion of the light output. The second repositionable system contains an alignment reference component and at least one optical workpiece held in a fixed position and a fixed orientation with respect to the alignment reference component. The second repositionable system is disposed to reflect, respectively, a first optical wavefront from the second portion of the light output (that has been transmitted through the first system) and a second optical wavefront from the same second portion through the first repositionable system towards the wavefront sensor. The apparatus additionally includes a positioner configured to simultaneously change i) at least one of a position and an orientation of the alignment reference component and ii) at least one of a position and an orientation of the at least one optical workpiece. In a specific case, the apparatus may be complemented with a mounting substrate installed across the axis and separated from the wavefront sensor by the first repositionable system. When so structured, the configuration of the apparatus satisfied one or more of the following conditions: a) the alignment reference component includes at least one of a reflective hologram attached to the mounting substrate, a reference surface of an optical element holder attached to the mounting substrate, and a reference surface of an optical element in the optical element holder attached to the mounting substrate; b) the at least one optical workpiece is affixed to the mounting substrate; c) the at least one optical workpiece includes a plurality of optical workpieces, each workpiece held in a fixed position and orientation with respect to the alignment reference component; d) the at least one optical workpiece and the alignment reference component are removably affixed in the mounting substrate; and e) the positioner is operably cooperated with the mounting substrate to change the at least one of position and orientation of the alignment reference component and the at least one optical workpiece simultaneously while changing at least one of position and orientation of the mounting substrate. Alternatively or in addition, the apparatus may be configured such that at least one optical workpiece is held in an opening defined through the mounting substrate, and/or further include a reference reflector positioned to receive light from the second wavefront through the at least one optical workpiece and reflect said light back onto itself, through the at least one optical workpiece, the first repositionable system, and into the wavefront sensor.

Related embodiments also provide an apparatus (for measuring an optical wavefront representing an optical workpiece) that includes a wavefront sensor; a first repositionable system that contains a first alignment hologram, a first measurement hologram, and a second alignment hologram and that is disposed across the axis of the apparatus such as to form a primary alignment wavefront by reflecting a first portion of light output from an optical wavefront delivered from the wavefront sensor and incident onto the first alignment hologram, and to transmit a second portion of said light output through the second alignment hologram. The apparatus additionally includes a second repositionable system that contains a reflective hologram (disposed across the axis to reflect light from the second portion through the first optical system to form a secondary alignment wavefront propagating through the first repositionable system towards the wavefront sensor) and tangible fiduciary references outside of the reflective hologram (here, such fiduciary references are structured to spatially align the workpiece with respect to the second repositionable system). In a specific case, the wavefront sensor may include an optical interferometer and/or the first repositionable system may be disposed at a location at which said optical wavefront delivered from the wavefront sensor is either spatially-diverging or spatially converging and/or the reflective hologram may be configured to include at least one reflective diffraction pattern designed to form the secondary alignment wavefront that represents at least one of the spatial tilt, azimuthal angular deviation, transverse shift, and longitudinal shift of the second repositionable system with respect to the axis. Additionally or in the alternative—and in any implementation of the apparatus—the first measurement hologram may be made a transmissive hologram configured to transform the incident optical wavefront into an aspheric optical wavefront and/or the first repositionable system may include a first stand-alone repositionable component containing the first alignment hologram and a second stand-alone repositionable component containing the first measurement hologram (here, the first measurement hologram is configured to transform the incident optical wavefront into an aspheric optical wavefront).

Embodiments additionally provide a method for measuring an optical wavefront characterizing an optical workpiece. Such method includes a step of determining a misalignment of a first system with respect an axis with the use of a substantially-spherical optical wavefront incident thereon from a wavefront sensor (here, the first system contains at least a first alignment hologram, a first measurement hologram, and a second alignment hologram) and a step of redirecting first and second optical wavefronts, formed by transmitting the substantially-spherical optical wavefront respectively through the first and second alignment holograms, towards a second system containing a mounting substrate and an alignment reference component disposed in a first opening of the mounting substrate. The method additionally include steps of forming reflected first and second optical wavefronts (by respectively interacting the first and second optical wavefronts with the optical workpiece fixatedly positioned in a second opening of the mounting substrate and the alignment reference component) and propagating the reflected first and second optical wavefronts through the first system towards the wavefront sensor. The method further involves spatially aligning the alignment reference component affixed at the mounting substrate to eliminate at least one of the spatial tilt, azimuthal angular deviation, transverse shift, and longitudinal shift of the alignment reference component with respect to the axis (by changing at least one of position and orientation of the mounting substrate with respect to the axis based on a measurement of light from the reflected second optical wavefront acquired at the wavefront sensor) and determining an error in the reflected first optical wavefront based on a measurement of light from the first reflected optical wavefront acquired at the wavefront sensor. Alternatively or in addition, the method may include a step of substantial nullification of the misalignment of the first optical system (by partially reflecting the substantially-spherical optical wavefront at the first alignment hologram of the first system towards the wavefront sensor to form a reflected wavefront) and/or a step of at least reducing the misalignment of the first system (by minimizing a figure of merit determined based on a measurement of a phase of the reflected wavefront at the wavefront sensor) and/or a step of spatially fixating a component of the first optical system with respect to the axis after said figured of merit has been minimized. (In the latter case, the process of determining the error in the reflected first optical wavefront may be carried out after the step of at least reducing the misalignment of the first system has been accomplished.) Alternatively or I addition, the method may be configured such that—when the wavefront sensor is an optical interferometer—at least one of the following conditions is satisfied: i) the process of determining the error in the reflected first optical wavefront includes determining a difference between a spatial profile of the reflected first optical wavefront that has transmitted through the first system towards the interferometer and a spatial profile of a reference optical wavefront generated internally to the interferometer; ii) the process of spatially aligning the alignment reference component includes forming alignment optical interference fringes by optically interfering (at an output of the optical interferometer) the reflected second optical wavefront that has transmitted through the first system and the reference optical wavefront; and iii) the process of at least reducing the misalignment includes reorienting the component of the first system to substantially eliminate at least one of the spatial tilt, azimuthal angular deviation, transverse shift, and longitudinal shift of such component with respect to the axis based on transformation of the optical interference fringes formed at the output of the optical interferometer. In at least one implementation of the method, the first system includes first and second spatially-distinct and separable from one another components (here, the first component contains one or more of the first alignment hologram, the second alignment hologram, and the first measurement hologram while the second component contains remaining of the first alignment hologram, the second alignment hologram, and the first measurement hologram). In substantially any implementation of the method, the steps of redirecting and spatially aligning may be—and preferably are—carried out without a relative movement between the workpiece and the mounting substrate and without a relative movement between the alignment reference component and the mounting substrate. In substantially any implementation of the method, the step of redirecting the second optical wavefront by interacting said second optical wavefront with the alignment reference component may include at least one of (a) reflecting the second optical wavefront by a reflective hologram contained in the second optical system; (b) reflecting the second optical wavefront at a reference surface of an optical element holder held in a respectively-corresponding opening of the mounting substrate; and (c) reflecting the second optical wavefront at a reference surface of an optical element mounted in the optical element holder held in the respectively-corresponding opening of the mounting substrate. In substantially any implementation of the method, the process of redirecting first and second optical wavefronts may include redirecting a plurality of measurement optical wavefronts (each of which is formed by transmitting the substantially-spherical optical wavefront through a plurality of the measurement holograms of the first system) and forming simultaneously a plurality of reflected measurement optical wavefronts (by respectively interacting each of the plurality of measurement optical wavefronts with a corresponding workpiece from a plurality of workpieces disposed in respectively-corresponding openings in the mounting substrate).

Embodiments of the invention additionally provide a related method for measuring an optical wavefront characterizing an optical workpiece with a wavefront sensor. Such method includes determining a misalignment of a first system with respect to an axis with the use of a substantially-spherical optical wavefront incident thereon from the wavefront sensor (here, the first system contains a first alignment hologram, a first measurement hologram, and a second alignment hologram); redirecting a first optical wavefront, formed by transmitting the substantially-spherical optical wavefront through the second alignment hologram, towards a second system containing at least one reflective hologram; forming a reflected first optical wavefront by interacting the first optical wavefront with the at least one reflective hologram; and aligning the second system with respect to the axis by reducing at least one of spatial tilt, azimuthal angular deviation, transverse shift, and longitudinal shift of the at least one reflective hologram by measuring an error of the reflected first optical wavefront (that has transmitted through the first optical system) with the wavefront sensor. The method further includes the steps of juxtaposing and affixing the optical workpiece with the second system in reference to visually-perceivable fiducial features of the second system; redirecting a second optical wavefront (formed by transmitting the substantially-spherical optical wavefront through the first alignment hologram) towards the second system to form a reflected second optical wavefront by interacting the second optical wavefront with the workpiece; and determining an error in the reflected second optical wavefront based on a measurement of light from the reflected second optical wavefront acquired at the wavefront sensor.

BRIEF DESCRIPTION OF THE DRAWINGS

The invention will be more fully understood by referring to the following Detailed Description of Specific Embodiments in conjunction with the Drawings, of which:

FIGS. 7A, 7B, and 7C provide schematic illustrations to the structure and operation of a related embodiment of the invention.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

The fundamental shortcoming persisting in related art comes from the demand for higher performance optical systems that take advantage of the ability to produce more complex optical elements, yet the existing methods for optical measurement of these elements (including their alignment in the measurement optical system(s)) suffer from either accuracy limitations (the alignment for optical testing requires six degrees of freedom) and/or are not fast enough to support volume production.

Figure 3:
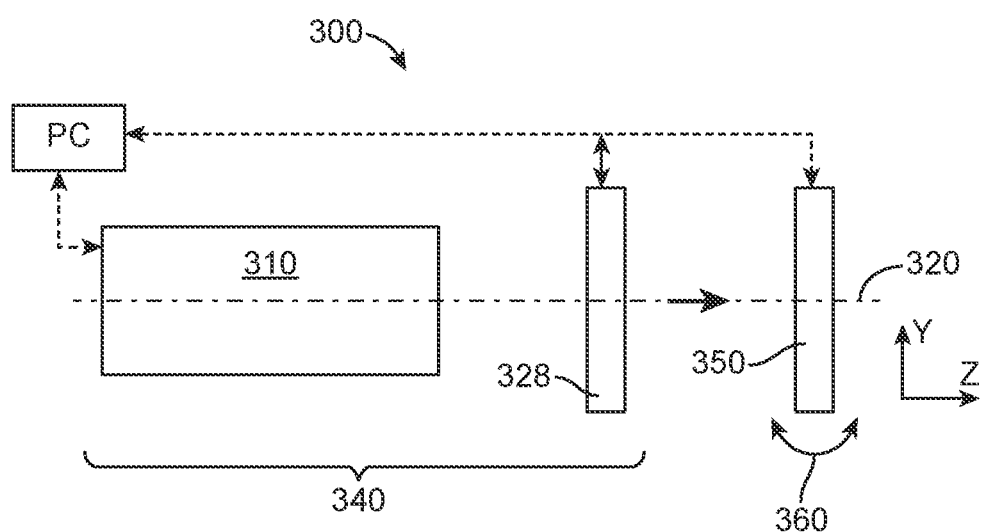
FIG. 3 schematically illustrates the measurement system configured according to the idea of the invention.

This problem is addressed by embodiments of the present invention that provide, in one example—in reference to the schematic of FIG. 3—an optical measurement system 300 containing a wavefront sensor 310 (in a specific case—the interferometer-based optical wavefront sensor), a first system containing a first optical system that includes a primary hologram 328 (which, generally, corresponds to the element 128 of the conventionally-structure measurement system), and a metrology frame 350 that may include or be cooperated with or carry a second optical system (the combination of the metrology frame with its contents is referred below as a second system). The combination of the contraptions 310 and 328 is denoted as 340—and, generally, such combination corresponds to the system 140 of FIG. 1. The axis of the system (and of the primary hologram 328, when the primary hologram is properly aligned) is denoted as 320, as is associated with the z-axis of the local system of coordinates. According to the idea of the invention, the metrology frame (with or without the second optical system) is judiciously configured for alignment and measurement of the workpiece under test (once such workpiece is juxtaposed with the metrology frame) with respect to the testing wavefront emanating from the first optical system 328. For the purposes of this disclosure and the appended claims, the term wavefront is generally defined according to the common understanding of this term in related art—as a surface that is transverse to the wavevector of a monochromatic wave and in which such wave maintains the same, constant phase.

The metrology frame 350 may contain—depending on the specific implementation—the second optical system that includes an auxiliary or secondary CGH (disposed to reflect light back to the primary CGH 328) and/or a set of reference surfaces or tangible features (interchangeably referred to as datum surfaces or features) that are accurately manufactured, both in their shape and position. According to the idea of the invention, measurements performed with the use of the second optical system of the metrology frame 350 are used to define the position of the metrology frame with respect to the optical wavefront-sensor-based measurement system 340. In some cases, the unit under test UUT (not shown) is an aspheric surface which affects the shape of the wavefront upon reflection. Alternatively, the UUT could include a system or combination of multiple optical elements that affect the wavefront upon the transmission of such wavefront through this combination and/or upon reflecting such wavefront off of the combination while relative positions of the optical elements in such combination may be controlled with the use of employed mounting hardware.

Preferably, the wavefront sensor and the first and second systems are operably cooperated with the programmable computer processor (indicated in FIG. 3 as PC) that is cooperated with the tangible non-transitory storage medium carrying thereon program code that, when loaded onto the processor, governs at least the acquisition of optical data from the wavefront sensor and/or the relocation/repositioning/reorientation of at least one of the first and second systems.

Datum or reference or fiduciary features on the metrology frame 350 (such a visually-perceivable markings, surface relief or structures, or other tangible indicia) are used to judiciously define the required position of the workpiece in and/or in reference to the metrology frame. As will be understood from the following disclosure, in one implementation the related measurement procedure of the workpiece UUT with the use of the system 300 may generally involve:

A step of calibrating the measurement system 340. This calibration procedure typically addresses the calibration of the wavefront sensor 310 (unless the wavefront sensor 310 has been already pre-calibrated) and at least the determination or measurement of misalignment of the primary CGH 328 with respect to the wavefront sensor 310. (The physical correction of such misalignment, resulting from mutual repositioning and/or reorientation of the CGH 328 at this step is considered to be optional);

A step of alignment of the metrology frame 350 (which has been already structured to have datum features and/or the secondary CGH to be used for alignment of the UUT or optic under test)—with or without contents of the metrology frame—with respect to the primary CGH 328 using the predetermined alignment patterns;

Juxtaposing the optical workpiece or UUT (not expressly shown in FIG. 3) with the metrology frame 350 and aligning it with respect to the metrology frame 350 using the available datum references for definition of all 6 degrees of freedom (DoFs); and Measuring the so-positioned/aligned optical workpiece with the use of optical wavefront(s) delivered to the metrology frame 350 from the sub-system 340.

After the measurement of a given optical workpiece has been accomplished, and in order to measure a new optic with identical prescription (which term conventionally denotes the definition of the ideal shape for an asphere or a parameter for a set of optical elements, as a skilled artisan knows), the first optical workpiece is simply removed from the metrology frame 350 and the new optic is inserted into the same metrology frame using the same datum references. To measure a new optical workpiece with new prescription, however, the primary CGH 328 must understandably be replaced (to generate a different testing wavefront corresponding to the new optical workpiece). Even in this case, however, if the required mounting features of the new optical workpiece are identical, then it is possible to use the same metrology frame configured according to the idea of the invention.

Advantages provided by embodiments of the current invention become clearer once the limitations of methodologies of measuring complex aspheric surfaces currently accepted and used by related art are considered. Currently used methods of measuring complex aspheric surfaces fall within several classes:

Precision profiling. Here, highly accurate machines are available that scan touch or optical probes over the surface to measure substantially any shape. If cost is not an issue, equipment is available that measures both optical surfaces and mounting interfaces to the precision required. The limitation here comes from the cost of the machines and the throughput. It can take many minutes to provide an accurate scan of even a small part and the machines are too expensive to achieve high rates with parallel measurement lines.

Optical scanning. Several technologies scan patches of interferometric measurements over the surface and combine them with software to determine the shape of the full surface. These machines have two limitations, any particular machine will be limited in the class of aspherics that it can measure—typically only axisymmetric parts. Since this methodology relies on scanning, the measurements and the data reduction are time consuming, to say nothing about difficulties for non-expert users to set up the required measurements such that they are assured accuracy.

Standard interferometry. Commercial systems are available that measure surfaces that have only a small departure from flat or spherical. These machines provide quick snapshot measurements that can achieve nanometer (nm) accuracy. The limitation of interferometry comes from the available dynamic range. Without the addition of additional optics or CGHs, the interferometer is limited to measuring a surface that has only a few micron departure from a reference spherical surface.

Interferometry with null correctors. The addition of a null corrector (another optical system that combines with the interferometer to give a null measurement for a particular shape) allows for the measurement of an aspheric surface with a standard interferometer. Classically, the null corrector comprises a set of lenses or mirrors, but nearly all modern null correctors utilize computer generated holograms. A new CGH must be designed and manufactured for each new aspheric surface. The CGHs have line patterns written onto them that use diffraction to change the wavefront shape from the spherical interferometer to the aspheric surface. CGHs written using modern lithographic techniques allow surface measurements of nearly any aspherical surface to nm accuracy.

Example 1

In further reference to FIG. 3, FIGS. 4A, 4B, and 4C provide a schematic illustration to an embodiment of the invention, in which the metrology frame 350 incorporates or contains or carries an auxiliary (or second, or metrology reference) optical system 418. The second optical system 418 includes at least one secondary or auxiliary holographic layer (in one specific case—at least one secondary hologram configured as an optical reflector).

Figure 1:
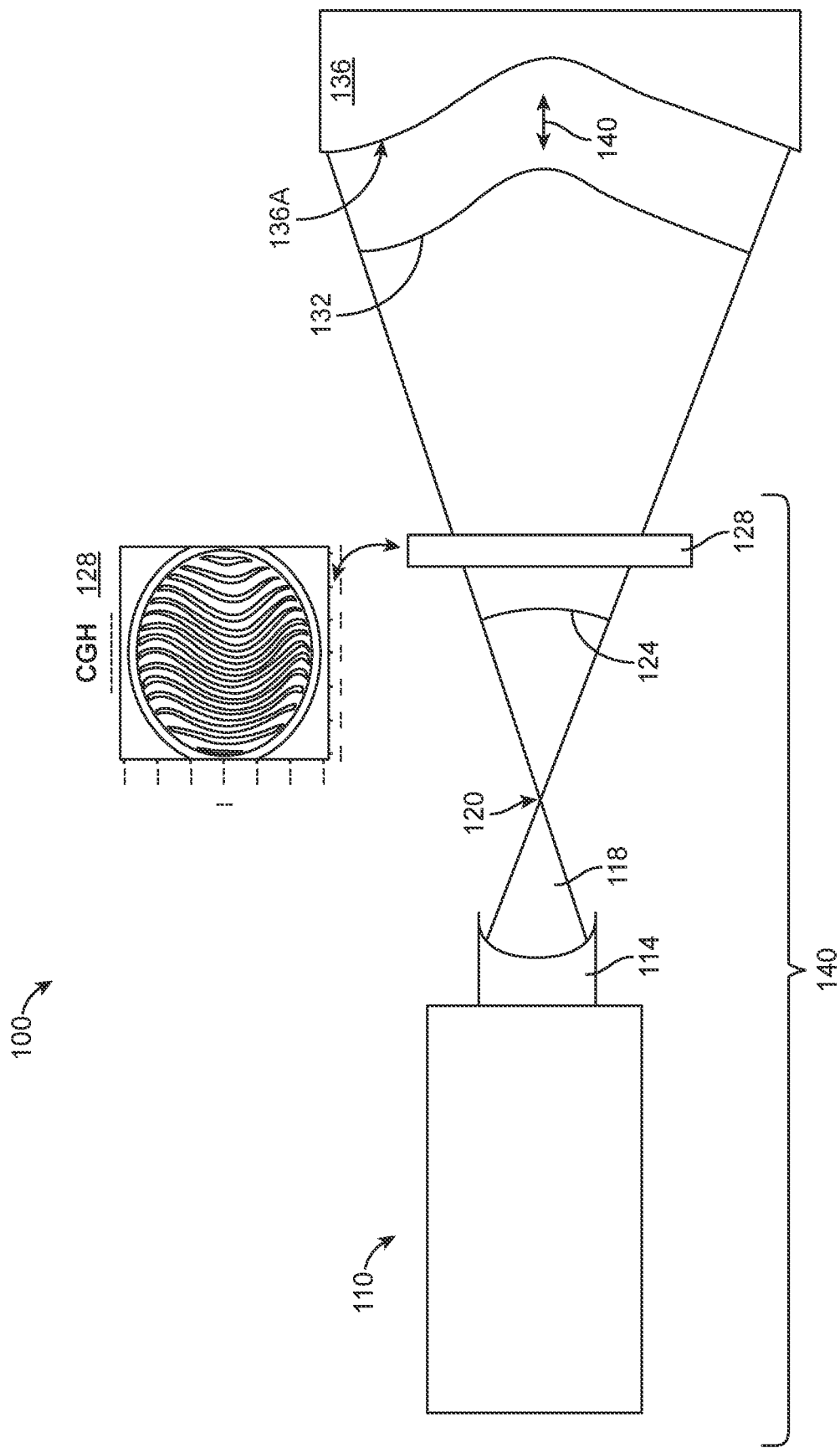
FIG. 1 schematically illustrates conventionally-configured methodology for assessing an optical wavefront representing an optical unit under test (a workpiece) with the use of a measurement system including and interferometric system and a holographic element (here, a CGH).
Figure 2:
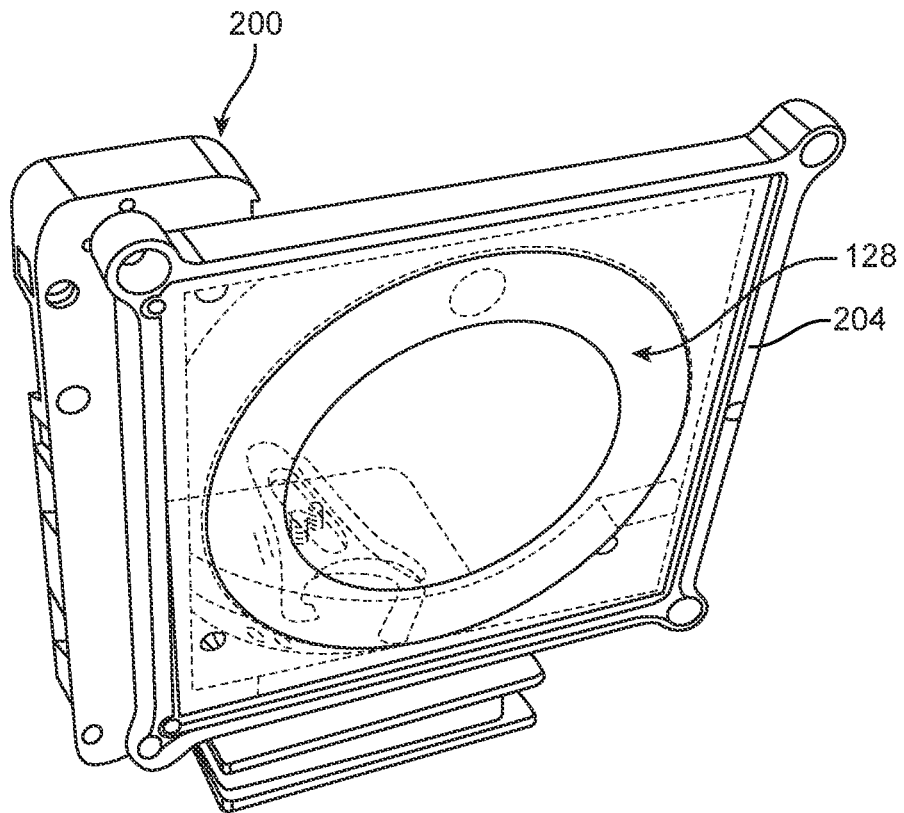
FIG. 2 shows a kinematic mount for repositionably-holding the CGH in a conventional measurement illustrated in FIG. 1.

Here, the primary optical system 428 (that contains an CGH with a holographically-defined reflective pattern and that corresponds to the element 128 of FIG. 1 and to the contraption 328 of FIG. 3) is kinematically mounted, as known in related art (see FIG. 2). However, according to the idea of the invention the system 428 can be modified as compared with the conventional component 128. In particular, the system 428 generally can be configured—as discussed in detail below—as a unitary, single-piece system or as a combination of at least two stand-alone sub-systems. In the latter case (which is in advantageous contradistinction with the way the element 128 is configured conventionally in related art), one of the at least two such stand-alone sub-systems includes a holographically-defined reflective pattern used for alignment of the system 428 with respect to the wavefront sensor (WS) (not shown) while another is used for measurement of an optical wavefront representing a workpiece or UUT disposed in precise spatial coordination with the metrology frame 350 using the datum features of the frame 350. (Examples of such datum features are provided by markings, surface relief, edges, or other fiducial elements.) In operation, the primary optical system 428 (whether it contains only one, single-piece system or a multi-piece system) of an embodiment of the invention in used in place of the component 328 of FIG. 3 or in place of the conventionally-employed component 128 of the system 100 of FIG. 1.

Pre-alignment or determination of misalignment of the primary hologram with respect to the chosen axis. In reference to FIG. 4A—and before the process of the measurement of the workpiece is carried out—the primary optical system 428 is preferably appropriately aligned with respect to the WS and/or axis 320—or at least its relative misalignment with respect to the WS and/or axis 320 is determined.

Alignment of the metrology frame with respect to the chosen axis. According to the idea of the invention, and referring now to FIG. 4B, the second optical system 418 is now added to the optical train to be separated from the WS by the system 428 such as to intersect a portion of the optical wavefront 424 that is transmitted through the first system 428. The second optical system 418 is housed or held in or carried by a dedicated harness system (such as an appropriate mounting hardware cell of the metrology frame 350) that includes tangible reference/datum features with respect to which position and/or orientation of the optical system 418 can be precisely ensured and/or determined). The second optical system 418 includes a plurality of reflective metrology reference holograms, 444. Such reflective metrology reference metrology holograms (not shown; representing diffractive patterns built into the body of the system 418) are configured to redirect light from test or measurement wavefront(s) arriving onto the system 418 through and from the system 428 by diffracting these arriving wavefront(s) in reflection and through the first optical system 428 and towards the WS. Once diffracted back to the system 428, the test or measurement optical wavefronts can be referred to as return or redirected test wavefronts 440, and, upon reaching the WS of the overall system, be measured to acquire and/or determine their spatial profiles with respect to the predetermined reference of the overall measurement system. A skilled artisan will readily appreciate that in one specific case when the WS is configured as an optical interferometer, the return optical wavefronts 440 are optically-interfered with a reference optical wavefront (formed internally to the interferometer, for example with the use of a Fizeau transmission sphere) and the difference between a given returned wavefront and the reference wavefront is then determined with the use of the measurement involving assessment of the resulting interferogram.

Accordingly, the alignment of the optical system 418 with respect to the optical system 428 (the misalignment of which with respect to the WS and/or the reference axis 320 has been already determined and preferably corrected) can be performed.

The metrology reference holograms 444 encoded in the optical system 418 are judiciously structured to provide for alignment of the system 418 by measuring all 6 degrees of freedom. The design of such metrology reference CGHs involves a tradeoff of the size of the holographic patches, the measurement precision for each DoF, and the dynamic range for each measurement. (Once the second optical system 418 containing multiple reference holograms 444, and with it—the metrology frame 350—has been aligned with respect to the axis 320, the next step of the measurement of the wavefront carrying the information about the workpiece under test can be accomplished, as discussed below in reference to FIG. 4D.)

Figure 4A:
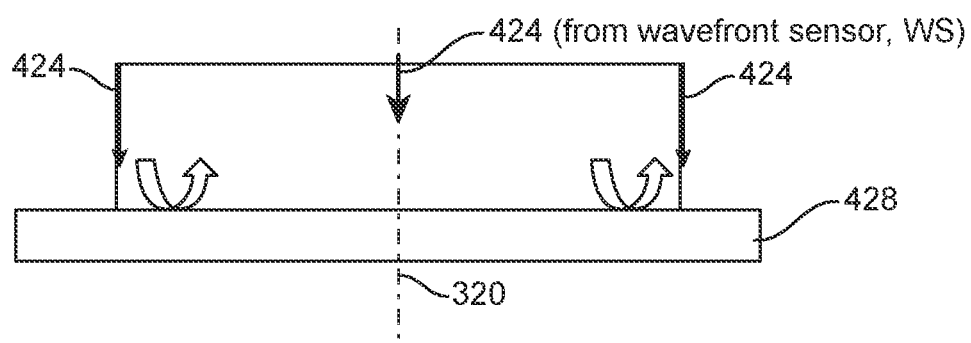
FIGS. 4A, 4B, 4C, and 4D provide an illustration to the methodology of alignment of optical components of an embodiment of the system of the invention and the following measurement of the UUT or workpiece with the use of such system.
Figure 4B:
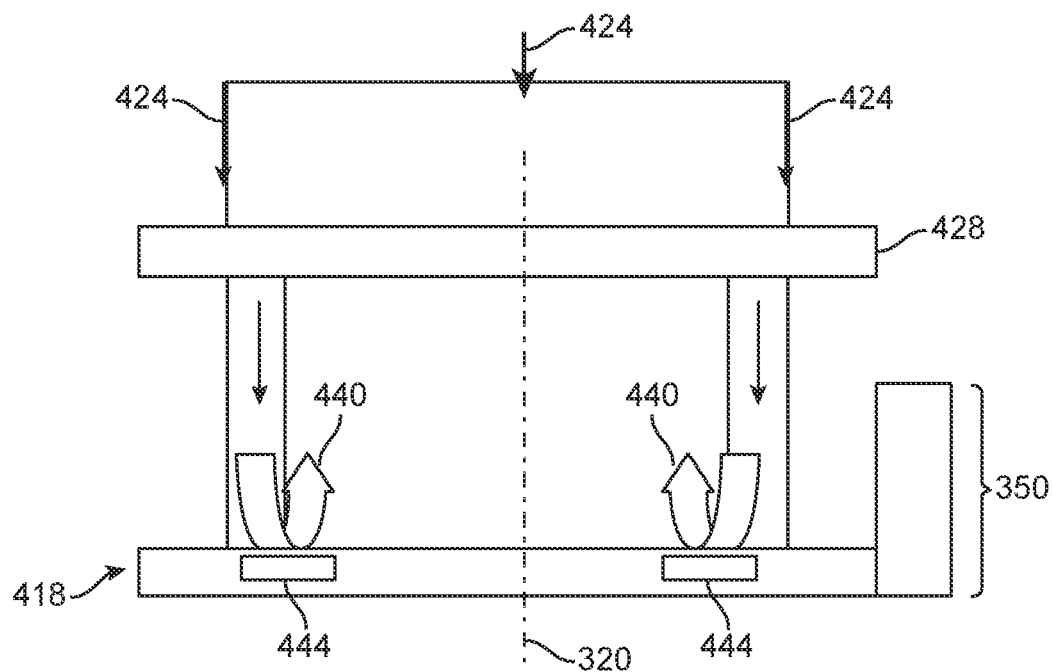
Figure 4C:
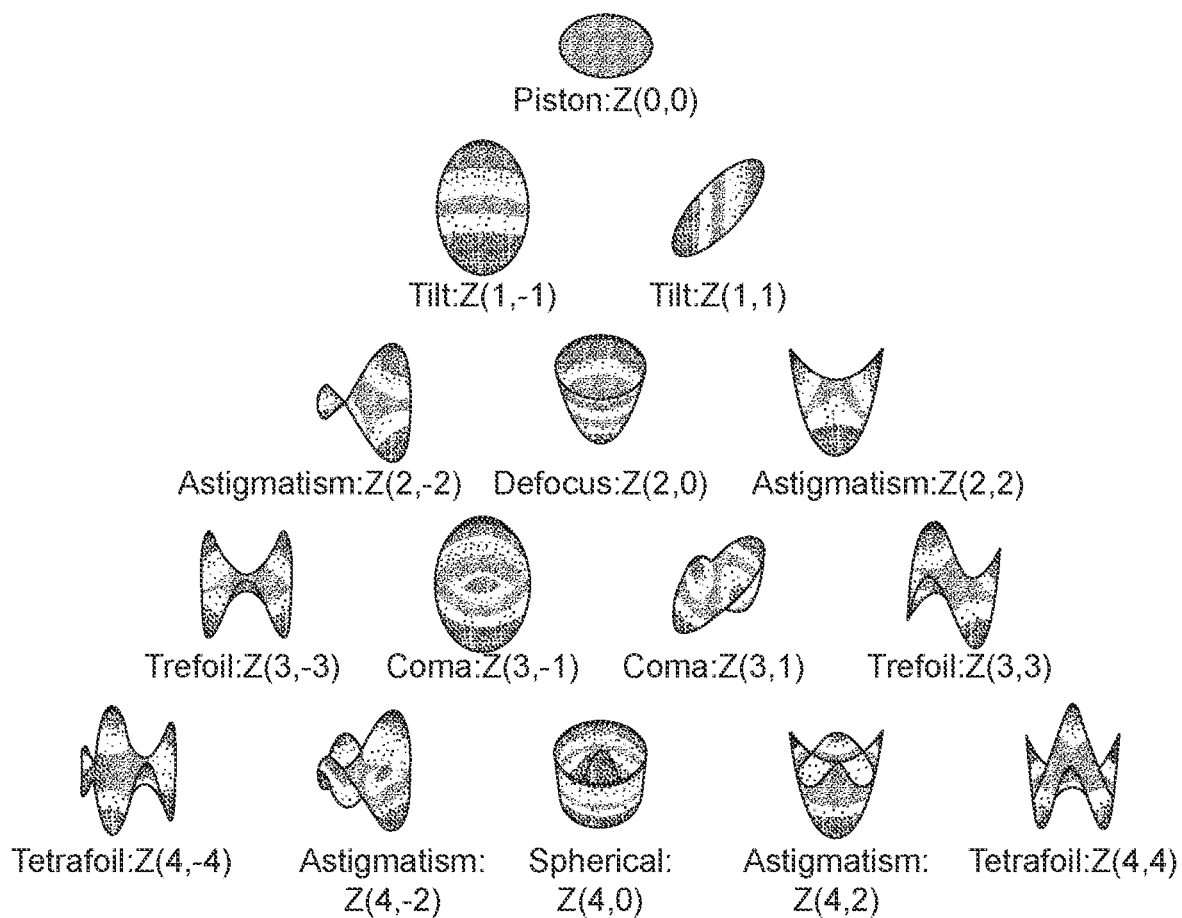

Referring again to FIG. 4B and considering the illustration of representation of various optical aberrations with the use of Zernike polynomials in FIG. 4C, in one specific implementation, the metrology frame 350 may be structured to include the second optical system 418 that contains or carries an auxiliary CGH 444 configured as a diffractive element simulating a spherical (for example, concave) reflector. In this case, the use of the returned-by-the-system 418 wavefront 440 improves the quality of alignment of the system 418 (as compared with the alignment based on reflection off of the tooling ball, known and currently utilized in related art). For reflections from a single spherical surface, it is impossible to discern tilt of the surface from decenter. (Due to the symmetry of the spherical ball, the tilt and decenter have exactly the same effect on the wavefront reflected from the tooling ball.)

However, by implementing the idea of the invention the degeneracy of the conventional tooling sphere or tooling ball can be addressed by optionally configuring the auxiliary CGH 444 in the optical system 418 to produce a wavefront with a higher-order spatial profile; see FIG. 4C. For example, spherical aberration (or Z(4,0), in Zernike terms) can be applied to a flat reflective surface, along with the matching wavefront from the measurement hologram. The interferometer will measure a null (ideal wavefront) for the case of alignment. If the CGH of the optical system 418 is tilted (for example, as a result of angular misalignment of the metrology frame 350 with respect to the axis 320), then the interferometer will measure the tilt. If the CGH-based reflector 444 of the secondary system 418 is translated or shifted laterally with respect to the direction of light propagation—such as axis 320 (as a result of the respective translation of the metrology frame 350), then the interferometer will measure coma (or Z(3,1) and Z(1,3), in Zernike terms). The amount of coma is proportional to the lateral shift.

Indeed, the interferometer measures the difference between the spatial profile of the optical wavefronts reflected by the CGH of the system 418 and that of the reference optical wavefront generated at the interferometer. The low order components can be decomposed (for the case of circular data sets) into Zernike polynomials. Even Zernike polynomials are defined as $$Z_n^m(\rho,\varphi)=R_n^m(\rho)\cos(m\varphi)$$

and odd Zernike polynomials are defined as $$Z_n^{-m}(\rho,\varphi)=R_n^m(\rho)\sin(m\varphi),$$

where m and n are non-negative integers. $\rho$ is the normalized radial distance and $\varphi$ is the azimuthal angle in radians.

$$R_n^m(\rho) = \sum_{k=0}^{(n-m)/2} \frac{(-1)^k(n-k)!}{k!\left((n+m)/2-k\right)!\left((n-m)/2-k\right)!}\rho^{n-2k}$$

Figure 9A:
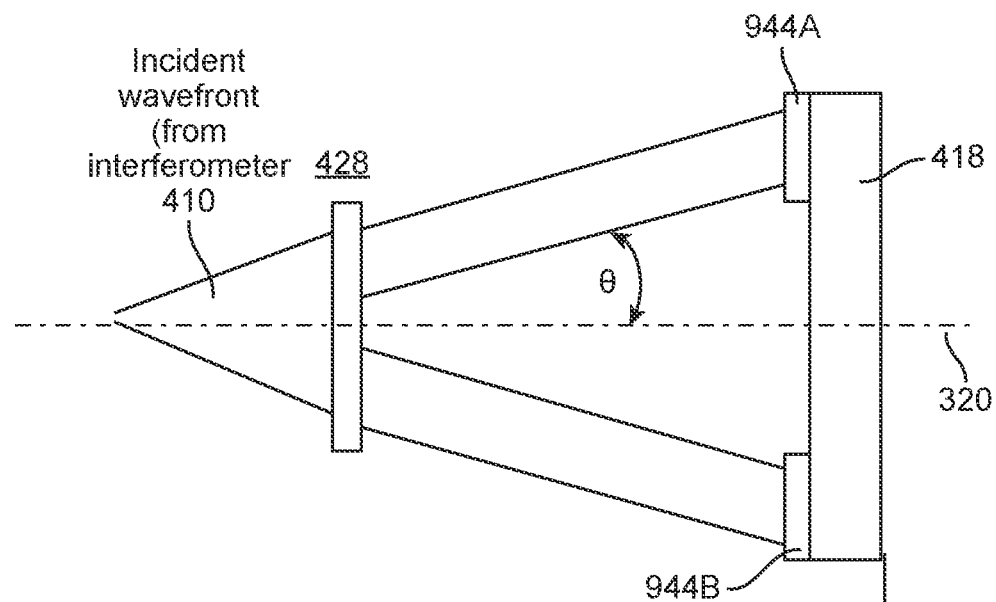
FIGS. 9A and 9B schematically illustrate specific geometry of the second optical system of the embodiment of the invention configured for determination of the axial displacement of the metrology frame of the invention.
Figure 9B:
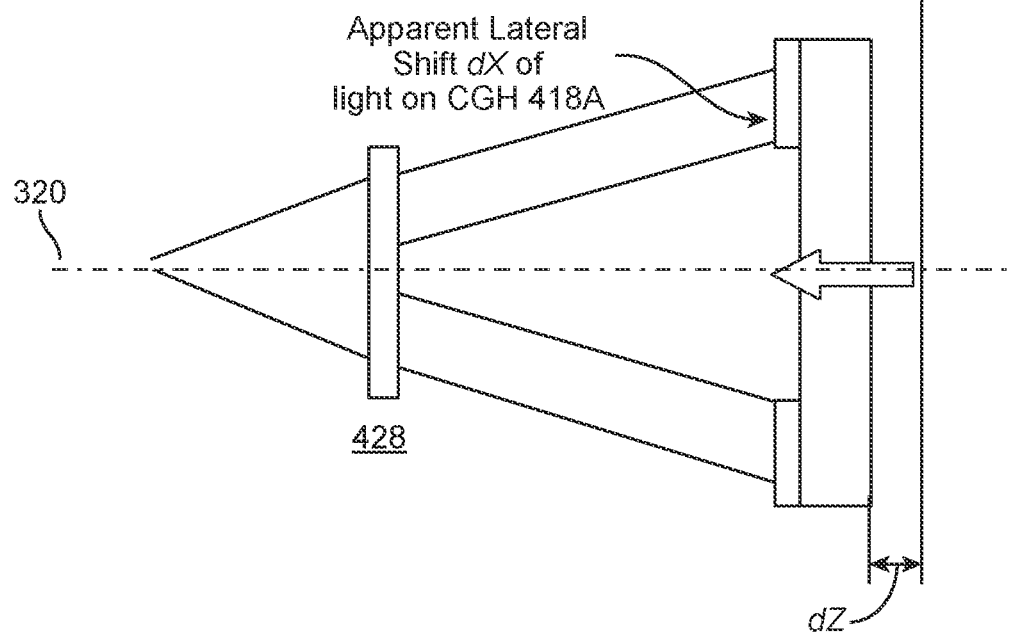

While the longitudinal shift (axial displacement of the CGH 444 of the system 418, together with the metrology frame 350) along the direction of the light propagation (axis 320) will have no effect, such axial displacement can be determined using specific geometry of the optical system 418 as illustrated in the example of FIGS. 9A, 9B (in a spatially diverging wavefront delivered from the optical system 428 to the optical system 418). In FIGS. 9A, 9B only the optical system 418 of the metrology frame is illustrated for simplicity. This geometry couples, links the axial motion of the system 418 into relative lateral measurements of first and second specifically-designed metrology reference holograms 444—as shown, the reflective CGHs 944A, 944B of the system 418 that are spatially separated from one another and the position and orientation of which does not change with respect to the optical system 418. (In one embodiment, the optical system 418 is configured as a glass plate carrying the reflective CGHs 944A, 944B.)

The shift of each reflective CGH 944A, 944B is a function of the off-axis distance, angularly represented as θ. The lateral shift of the reflection CGH 944A, 944B with respect to the wavefront comes from simple geometry, and can be calculated as Δx=Δz tan(θ), Δz being an axial (longitudinal) shift of the system 418. Understandably, the average lateral Δx motion as measured provides the net lateral motion or shift and the difference between the two is used to calculate the axial motion or shift of the metrology frame 350

Figure 4D:
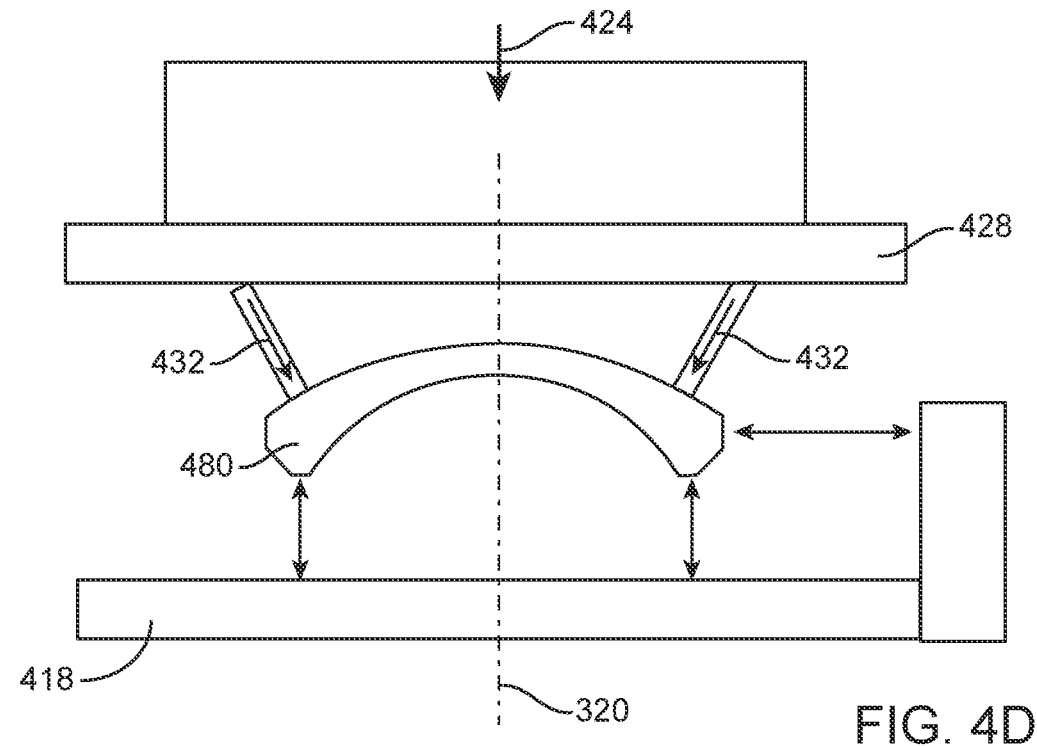

Once the secondary optical system 418 containing multiple reflective holograms 444 (among which there may be CGHs 944A, 944B) and with it—the metrology frame 350—has been aligned in reference to the axis 320, the measurement of the wavefront representing the UUT 480 can be carried out. Referring now to FIG. 4D, at this step the UUT or workpiece 480 is positioned in/located in/juxtaposed with the (now aligned in reference to axis 320) metrology frame 350 in the predetermined orientation with respect to the fiducial features of the frame 350. Appropriate transmissive holograms (or hologram patches) of the optical system 428 are then used to form the testing or measurement optical wavefront 432. (As was already alluded to during the discussion of the system 100, the testing optical wavefront preferably has spatial profile substantially approximating the expected spatial profile of the surface of the UUT 480. Therefore, the corresponding CGH patches of the system 428 should be designed to produce such a wavefront.) The wavefront 432 is then delivered to the UUT affixed in the frame 350 in reference to its fiduciary features and, upon reflection from the UUT 480, is delivered in transmission through the optical system 428 to the interferometer for the determination of a deviation (or difference) between the wavefront 432 reflected by the UUT and the reference wavefront (that is formed internally to the interferometer).

Example 2

Figure 5A:
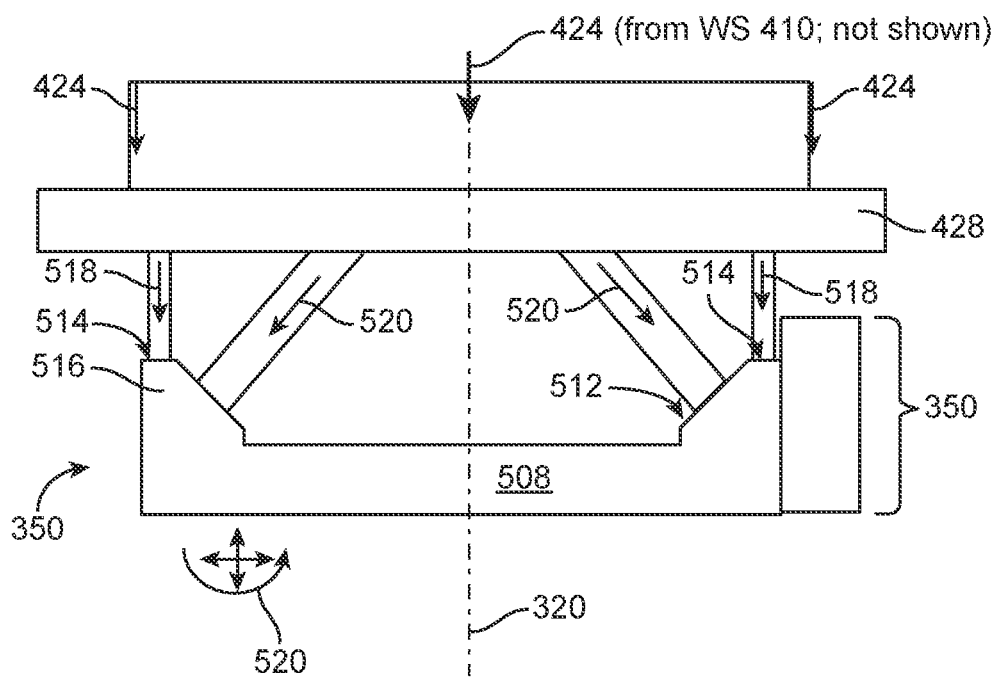
FIGS. 5A and 5B provide illustration to the methodology of alignment of optical components of a related embodiment of the system of the invention and the following measurement of the UUT with the use of such system.
Figure 5B:
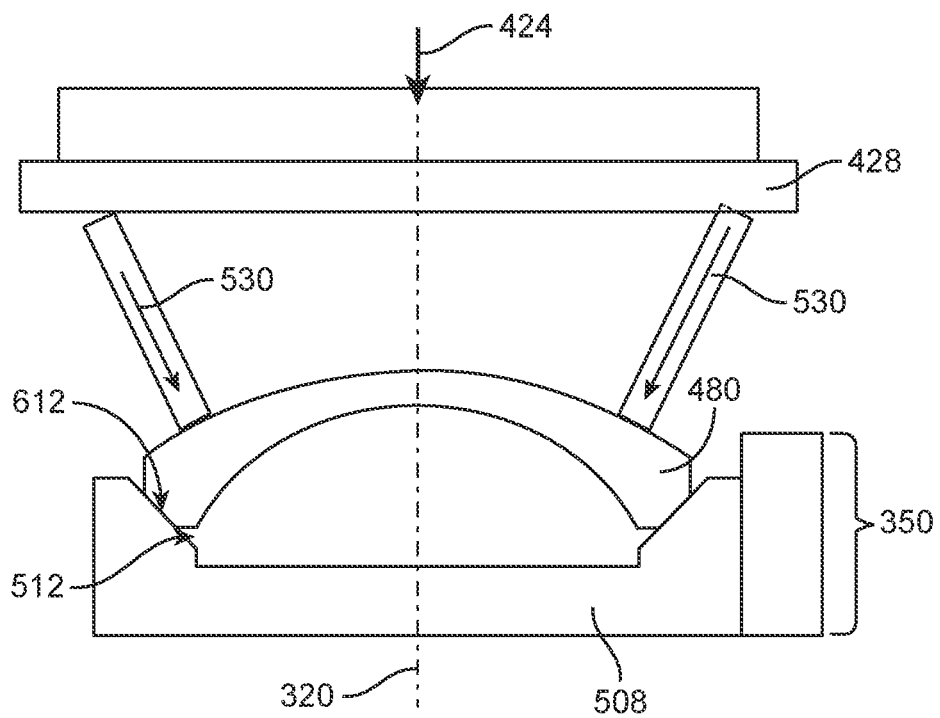

FIGS. 5A and 5B illustrate a related embodiment, in which the metrology frame 350 incorporates an optical component mount or holder 508 judiciously configured to incorporate specific fiduciary or datum structures and/or features 512, 514. In one example, such datum structure(s) include(s) a conical surface 512 precisely machined (for example, via diamond turning) at the internal side of the wall 516 (of the mount 508) that is dimensioned to accommodate the UUT to be tested, and/or a flat surface 514. As shown schematically in FIG. 5A, the mount 508 is accurately aligned with respect to the first optical system 428 before the optic (UUT) under test 480 is installed in the mount 508 in reference to and with the use of the same datum features 512. This alignment is performed with the use of the alignment optical wavefront(s) 518, 520 formed at the optical system 428 as a result of interaction of the incident optical wavefront 424 with the appropriately configured transmissive alignment holograms (or hologram patches; not expressly shown) of the system 428. As shown here, the fiduciary surfaces 512, 514 are used to substantially retro-reflect the respective incident wavefronts 520, 518 back to the WS through the optical system 428.

In the illustration of FIG. 5B, the UUT 480 to be tested is structured to be equipped with the datum feature of its own—in this example shown as the conical edge surface 522 that is substantially congruent with the datum reference surface 512 of the mount 508—thereby facilitating and guaranteeing the correct installation of the UUT 480 in the mount 508 and automatic alignment with respect to the measurement optical wavefront 530 that arrives from the optical system 428 as a result of diffraction of the incident wavefront 424 at the appropriate transmissive measurement hologram patches of the system 428. Once the workpiece or UUT 480 is juxtaposed with the mount 508 that is carried by the pre-aligned (at the step of FIG. 5A) metrology frame 350, the retro-reflection of the testing wavefronts 530 (produced by yet another set of holographic patches of the system 428; not shown) through the system 428 towards the WS gives rise to interferograms representing the deviation of the light-reflecting surface of the workpiece 480 from the testing wavefront(s) 530.

Example 3

Figure 6A:
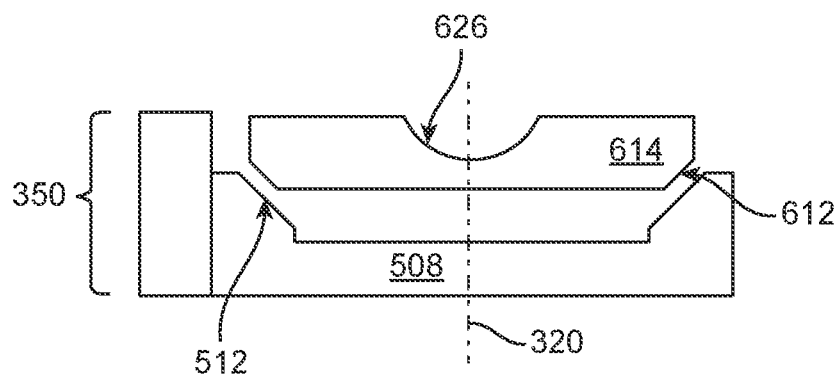
FIGS. 6A, 6B, and 6C provide illustration to the methodology of alignment of optical components of yet another related embodiment of the system of the invention and the following measurement of the UUT with the use of such system.
Figure 6B:
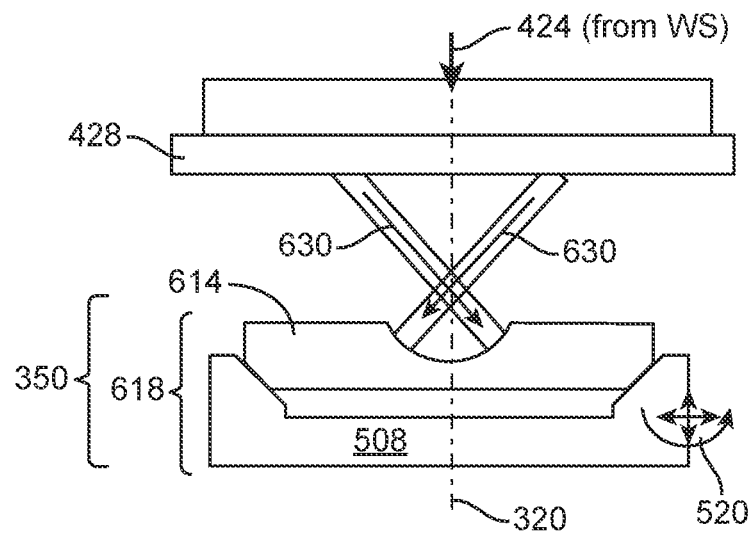
Figure 6C:
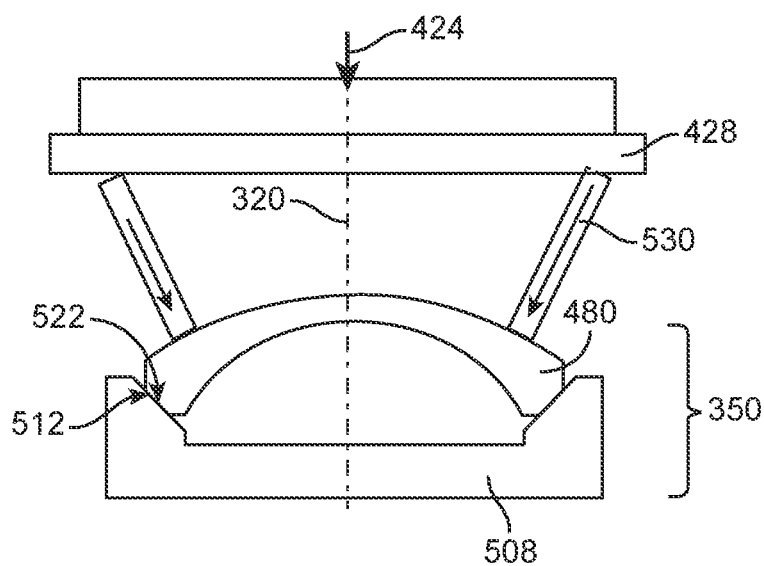

In yet another related embodiment- and in reference to FIGS. 6A, 6B, and 6C—the procedure of alignment of the metrology frame 350 in reference to the optical system 428 is accomplished with the use of a surrogate optical component 614. The surrogate component 614 is judiciously structured to possess not only datum (reference) feature(s) 612 that are substantially identical to and/or congruent with the datum features (see 512) of the mount 508 and of the UUT to be tested, and also has a pre-determined structural features (such as a reflective surface 626) dimensioned to be interrogated with the use of the optical alignment wavefront 630 that are generated at the appropriately configured hologram patches in the first optical system 428 and that are configured for use in the alignment portion of the procedure. The surrogate optic 614 is held in the mount 508 with the use of the mutually-matching fiduciary features 612, 512 (FIG. 6B) to form a combination 618. The misalignment of the combination 618 with respect to the system 428 is assessed with the use of the optical wavefront 630 returned in reflection from the surface 626 and through the system 428 into the interferometer (not shown). The metrology frame 350 (and with it, the mount-surrogate-optic combination 618) is then aligned, 520. Thereafter, the surrogate optic 614 is simply replaced with the UUT 480 using the identical surface to define its position in the mount 508, for interferometric measurement with the use of appropriate measurement wavefronts 530 generated at the corresponding transmissive holograms of the system 428.

The CGH 428 can generally be fabricated from fused silica glass substrate with an appropriate line pattern defined according to the simulations of diffraction of light and etched into the substrate to define required holographic pattern(s). Some of these patterns are configured to form alignment wavefronts 630 (that are designed to reflect off the surfaces manufactured onto the surrogate 614) from the incident wavefront 424. The simplest of the surfaces 626 are spherical or flat, but in some implementations the use of more complex shapes such as those described above may prove to be beneficial.

Notably, implementations of the system of the invention discussed above are not mutually exclusive. For example, a second optical system held in or being part of the metrology frame and used in addition to the first system 428 generally may include at least one of the systems 418, 508, 614, 618 that is/are used for the corresponding alignment and metrology steps.

Example 4

Mass production of high-performance optical systems (such as the advanced cameras in current generation cell phones) is enabled by glass and plastic molding technologies. Current measurement methods are proven to be too slow and expensive to measure each part by itself, so a manufacturers must control the process very tightly to ensure that defective parts are not built up into the assembly. Understandably, there exists an economic premium for measuring a higher fraction of the optical elements and subsystems.

A related embodiment of the invention is judiciously configured to permit the user to carry out simultaneous (a one-step) alignment of multiple UUTs (or workpieces) as well as simultaneous measurement of the wavefronts representing these UUTs regardless of whether these UUTs are identical or different from one another. This approach is now described in reference to FIGS. 7A, 7B, and 7C.

Here, according to the idea of the invention, the metrology-frame-based measurement methodologies described above are used for high-volume measurement of small optical elements, surfaces, and/or systems. Specifically, multiple—and differing from one another—optical components or systems to be measured can be placed using their fiduciary or datum surfaces to a custom mount or carrier possessing fiduciary interfaces matching and mating with those of multiple parts at the same time. High measurement throughput for the overall system is envisioned to be enabled using several carriers, so while one is being loaded, one can be measured, and another one can be unloaded. High accuracy is achieved with the intrinsic accuracy provided by the wavefront-based sending coupled with active alignment using fiduciary elements (such as, for example, a CGH).

The described approach turns on the realization that standardization for the mounting interface for multiple UUT components can be achieved with the use of the above-described metrology platform that supports such multiple UUT components with an ensemble of precision "seats" matching the final interfaces for the UUTs.

As shown, a plurality 710 of optical UUTs 710-1 . . . 710-N (which includes at least one optical UUT 710-i) and an alignment reference component 714 are disposed in a spatially-stable and (at least for the duration of the alignment and measurement steps of the process) spatially-invariable relationship with respect to one another. This is achieved by, for example, affixing the optical UUT(s) as well as the alignment reference component in or juxtaposing these elements with a single, common mounting tray 720

In one non-limiting example, the tray 720 can be formed by reaming an array of holes openings 724 in a metal plate or substrate while controlling the plate's flatness and positions and the dimensions of the mounting holes 723 down to microns. Then a set of surrogate optical component mounts or holders 508 (as described above) is fabricated that fit with tight tolerance into the reamed holes 724. The surrogate lens mounts 508 are provided with the fiduciary feature 522 that appropriately match and/or are congruent with the fiduciary interface surfaces 512 of the plurality 710 of UUTs. The individual UUTs 710-i can then be seated with required precision onto the respective surrogate mounts 508 that, in turn, are placed into the tray 720.

Depending on the specifics of the particular implementation, the alignment reference component 724 may be configured as at least one of the CGH 418, a reference mount similar to the mount 508, and the combination 618 of the surrogate optics and the mount 508.

As was already discussed above, the optical system 428 is generally equipped with multiple "patches" of the CGH having multiple patterns 736-1 . . . 736-N—in other words, the CGH system built into the system 428 is configured to provide for a measurement of multiple optical components at the same time, by transforming an optical wavefront incident upon it into a plurality of target wavefronts 740-1, . . . , 740-i, 740-N). In addition, the CGH contraption of the optical system 428 can include a holographic pattern A that is dedicated for alignment. The position control of the entire tray 720 as a rigid body is carried out based on the wavefront sensor measurements, while the alignment of the optics under test is controlled using the precise datum surfaces.

Figure 7C:
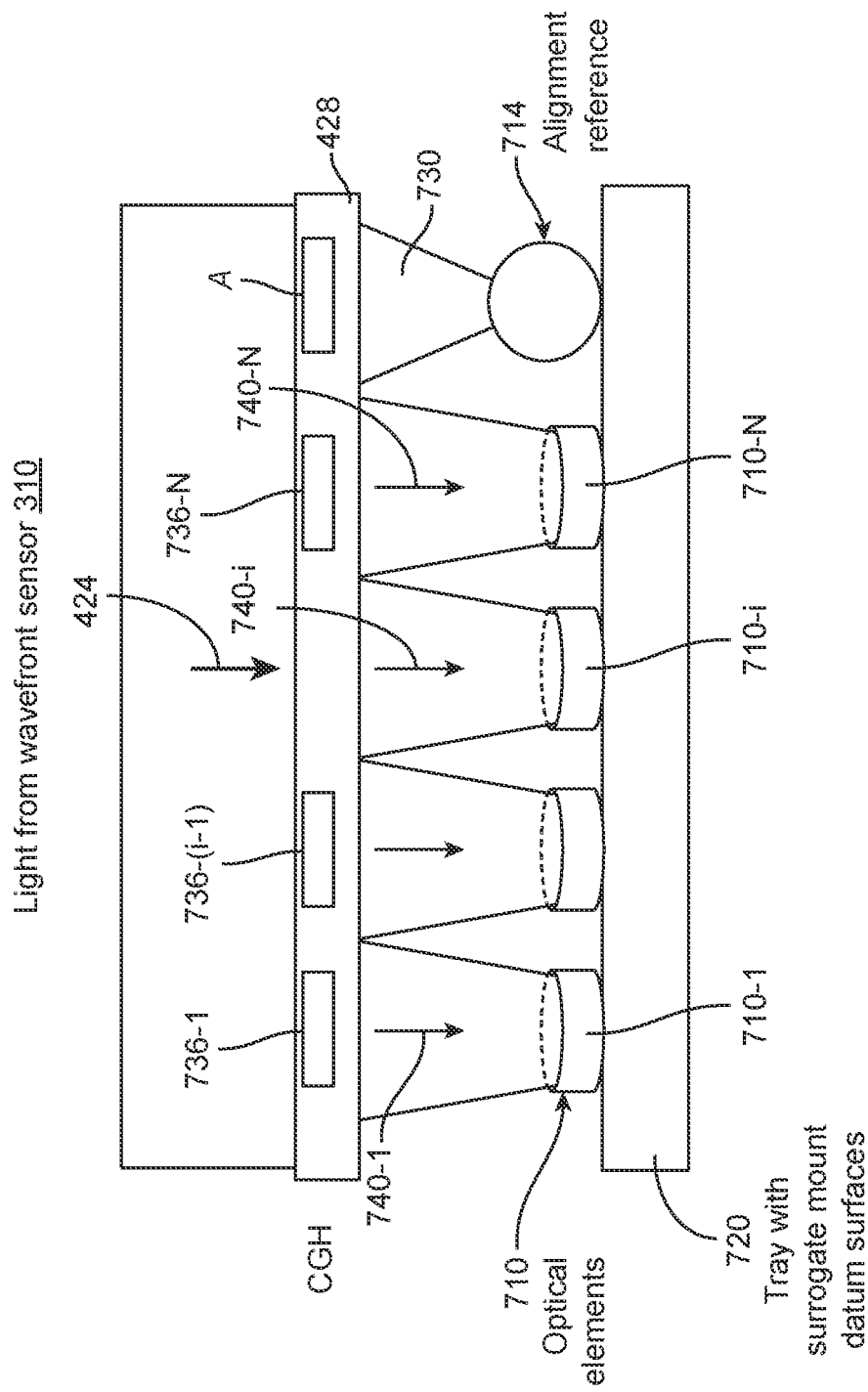

Accordingly—and referring now specifically to FIG. 7C—the process of simultaneous determination of errors in optical wavefronts representing UUT(s) affixed in the tray 720 is initiated by determining the spatial misalignments of the optical system 428 with respect to the wavefront sensor (now shown) as discussed, for example, in reference to FIGS. 4A and 6A, followed by the step of aligning the alignment reference component 714, affixed in the tray 720, with respect to an alignment wavefront 730 generated at the specific hologram contained in the system 428. (This process is similar to those discussed in reference to FIGS. 4B, 5B, and 6B—depending on the specific contents of the alignment reference component 714, and includes the repositioning/reorientation of the whole tray 720 with all its contents based on the measurements of the errors of the wavefront 730 reflected at the component 714 through the system 428 towards the wavefront sensor.)

A skilled artisan will readily appreciate that—once the component 714 fixed in the tray 720 is appropriately aligned—the alignment of the remaining optics (such as the UUT 710-i, for example) with respect to corresponding local axes of the respective wavefronts from the multiplicity of wavefronts (740-1 . . . 740-I, 740-N) is accomplished substantially automatically, without any additional precautions, and can be followed by the simultaneous measurements of the UUT(s) in the light delivered by the wavefront(s) (740-1, . . . , 740-I, 740-N) in a fashion discussed in reference to FIGS. 4C, 5C, 6C, for example.

Figure 8:
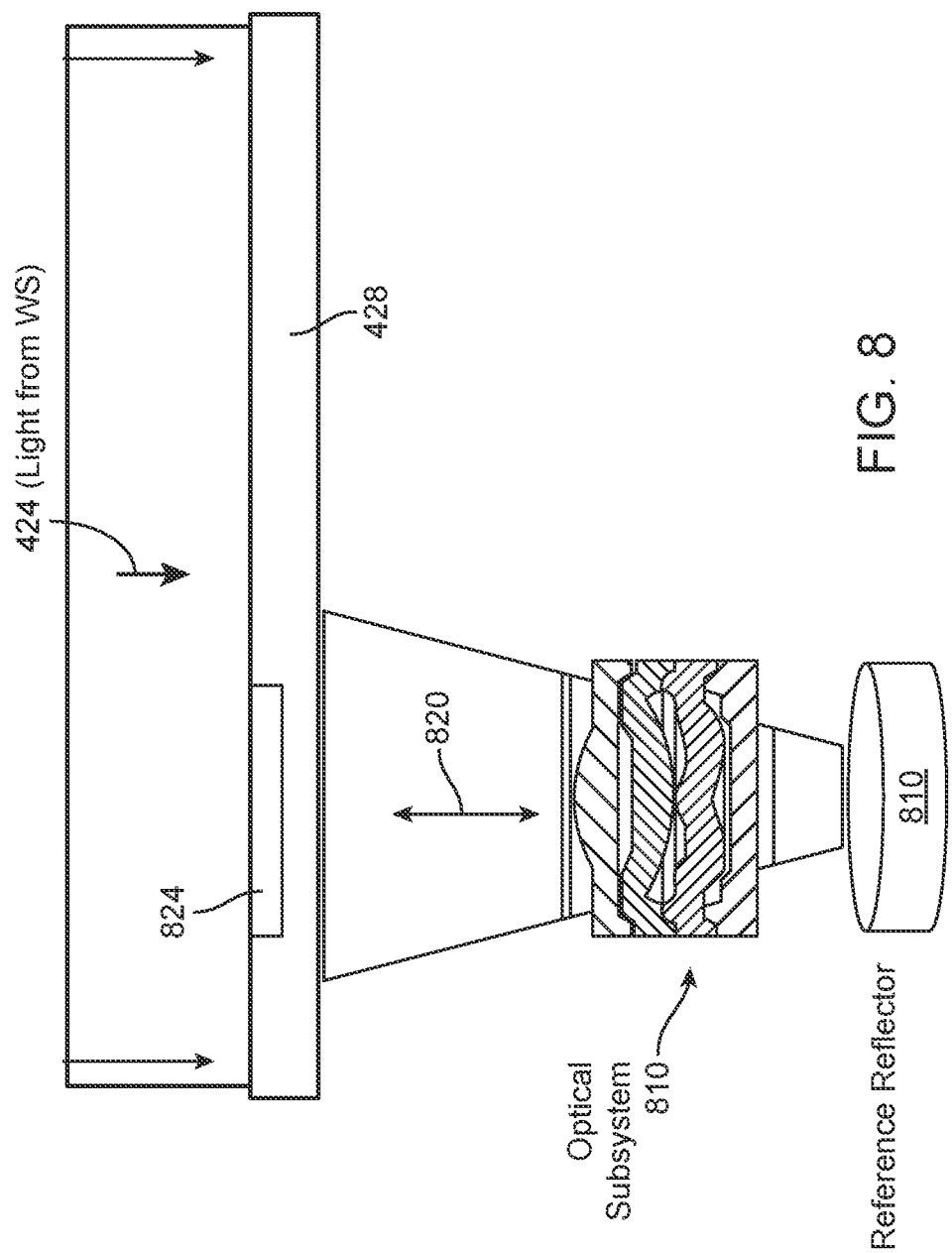
FIG. 8 depicts the measurement of a multi-element UUT in transmission.

Notably, an embodiment of the measurement system of the invention can be configured for empirical assessment of a wavefront representing a group 810 of optical components or systems at once (and containing the information not only about a spatial profile of a single surface but also aggregate information about at least one of the multiple surfaces present in such group and the distribution of indices of refraction of the components of such group). This implementation is schematically illustrated in FIG. 8, where the group 810 of individual optical components is shown to represent a lens system (that includes multiple individual lens elements) measured in the wavefront 820 formed in transmission from the wavefront 424, incident onto an appropriately-configured holographic patch 824 of the system 428. When the wavefront 820 is reflected at a reference reflector 830 upon having been transmitted through the group 810 and returned—again in transmission through the group 810 and then through the system 428—to the wavefront sensor 310, such wavefront contains information about the status of the lens system 810. In some embodiments, the reference reflector 830 may include a diffractive optical element.

A skilled person will now appreciate that, in order to carry-out the measurement discussed in reference to FIGS. 7A-7C and 8, the idea of the invention is implemented to provide an apparatus that includes a wavefront sensor and a first repositionable system containing a set of holograms (for example, a first alignment hologram, a first measurement hologram, and a second alignment hologram) and disposed across an axis of the apparatus such as i) to form a primary alignment wavefront by reflecting (with one of the alignment holograms) a first portion of light output from an optical wavefront that has been delivered from the wavefront sensor and that is incident onto the first repositionable optical system, and (ii) to transmit (through at least one of the remaining holograms) a second portion of such light output. The apparatus also contains a second repositionable system that includes an alignment reference component and at least one optical workpiece held in a fixed position and a fixed orientation with respect to the alignment reference component. Here, the second repositionable system is disposed to reflect, respectively, a first optical wavefront from the second portion of the light output and a second optical wavefront from the second portion of the light output through the first repositionable system back towards the wavefront sensor. The apparatus additionally includes a positioner configured to simultaneously change at least one of a position and an orientation of the alignment reference component and at least one of a position and an orientation of the at least one optical workpiece. Preferably, the apparatus includes a mounting substrate installed across the axis and separated from the wavefront sensor by the first repositionable system. In at least one case, the apparatus is configured to satisfy at least one of the following conditions: a) the alignment reference component includes at least one of a reflective hologram attached to the mounting substrate, a reference surface of an optical element holder attached to the mounting substrate, and a reference surface of an optical element in the optical element holder attached to the mounting substrate; b) at least one optical workpiece is affixed to the mounting substrate; c) at least one optical workpiece includes a plurality of optical workpieces, each of which is held in a fixed position and orientation with respect to the alignment reference component; d) at least one optical workpiece and the alignment reference component are removably affixed in the mounting substrate; and e) the positioner is operably cooperated with the mounting substrate to change at least one of position and orientation of the alignment reference component and the at least one optical workpiece simultaneously while and/or during the process of changing at least one of position and orientation of the mounting substrate. Alternatively or in addition, the apparatus may be configured such that at least one of the present optical workpieces is held in an opening defined through the mounting substrate, and to include a reference reflector positioned to receive light from the second wavefront through at least one optical workpiece and reflect the so-received light back onto itself, through the same optical workpiece, through the first repositionable system, and into the wavefront sensor.

Such a specific apparatus can be employed measuring an optical wavefront characterizing an optical workpiece as follows. The measuring procedure would include a step of determining a misalignment of the first repositionable system with respect the axis with the use of the substantially-spherical optical wavefront incident thereon from a wavefront sensor, followed by the step of redirecting first and second optical wavefronts (formed by transmitting the substantially-spherical optical wavefront respectively through the first and second alignment holograms) towards the second repositionable system that includes the mounting substrate and the alignment reference component disposed in a first opening of the mounting substrate. The reflected first and second optical wavefronts are then formed by interacting the first and second optical wavefronts with, respectively, the optical workpiece fixatedly positioned in a second opening of the mounting substrate and the alignment reference component (which is affixed to the mounting substrate), and propagating the reflected first and second optical wavefronts through the first repositionable system towards the wavefront sensor. The alignment reference component is then spatially aligned to eliminate at least one of the spatial tilt, azimuthal angular deviation, transverse shift, and longitudinal shift of the alignment reference component with respect to the axis by changing at least one of position and orientation of the mounting substrate with respect to the axis and based on a measurement of light (as performed by the optical detection system of the wavefront sensor) from the reflected second optical wavefront acquired at the wavefront sensor. Finally, a determination of an error in the reflected first optical wavefront is performed based on an interferometric measurement of light from the first reflected optical wavefront acquired at the wavefront sensor.

Features of the specific implementation(s) of the idea of the invention is described with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

A person of ordinary skill in the art will readily appreciate that references throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. Accordingly—as the skilled artisan will readily appreciate—while in this specification the embodiments have been described in a way that enables a clear and concise specification to be written, it is intended that substantially none of the described embodiments can be employed only by itself to the exclusion of other embodiments (to the effect of practically restriction of some embodiments at the expense of other embodiments), and that substantially any of the described embodiments may be variously combined or separated to form different embodiments without parting from the scope of the invention.

Embodiments of the invention have been described as preferably including a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The invention as recited in claims appended to this disclosure is intended to be assessed in light of the disclosure as a whole.

The invention claimed is:

1. An apparatus for measuring an optical wavefront representing an optical workpiece, the apparatus having an axis and comprising:
   a wavefront sensor;
   a first repositionable system containing a first alignment hologram, a first measurement hologram, and a second alignment hologram and disposed across the axis
      to form a primary alignment wavefront by reflecting a first portion of light output from an optical wavefront delivered from the wavefront sensor and incident onto the first alignment hologram, and
      to transmit a second portion of said light output through the second alignment hologram;
   and
   a second repositionable system that contains:
      a) an alignment reference component disposed across the axis to reflect light from the second portion through the second alignment hologram to form a secondary alignment wavefront propagating through the first repositionable system towards the wavefront sensor; and
      b) fiduciary references outside of the alignment reference component configured to spatially align the optical workpiece with respect to said fiduciary references.

2. The apparatus according to claim 1, wherein the wavefront sensor includes an optical interferometer.

3. The apparatus according to claim 1, wherein the first repositionable system is disposed at a location at which said optical wavefront delivered from the wavefront sensor is either spherical or collimated.

4. The apparatus according to claim 1, wherein the aligment reference component is configured to form the secondary alignment wavefront that represents at least one of spatial tilt, azimuthal angular deviation, transverse shift, and longitudinal shift of the second repositionable system with respect to the axis.

5. The apparatus according to claim 1, wherein the first measurement hologram is a transmissive hologram configured to transform said incident optical wavefront into an aspheric optical wavefront.

6. The apparatus according to claim 1, wherein the first repositionable system includes a first stand-alone repositionable component containing said first alignment hologram and a second stand-alone repositionable component containing said first measurement hologram, wherein the first measurement hologram is configured to transform the optical wavefront into an aspheric optical wavefront.

7. A method for measuring an optical wavefront characterizing an optical workpiece with a wavefront sensor, the method comprising:
   determining a misalignment of a first system with respect to an axis with the use of an optical wavefront incident thereon from the wavefront sensor,
      wherein the first system contains a first alignment hologram, a first measurement hologram, and a second alignment hologram;
   redirecting a first optical wavefront, formed by transmitting the optical wavefront through the second alignment hologram, towards a second system containing at least one alignment reference component;
   forming a reflected first optical wavefront by interacting the first optical wavefront with the at least one aligment reference component;
   aligning the second system with respect to the axis by reducing at least one of spatial tilt, azimuthal angular deviation, transverse shift, and longitudinal shift of the at least one alignment reference component by measuring an error of the reflected first optical wavefront, that has transmitted through the second alignment hologram, with the wavefront sensor;
   affixing the optical workpiece with the second system in reference to fiducial features of the second system;
   redirecting a second optical wavefront, formed by transmitting the optical wavefront through the first alignment hologram, towards the second system to form a reflected second optical wavefront by interacting the second optical wavefront with the optical workpiece; and
   determining an error in the reflected second optical wavefront based on a measurement of light from the reflected second optical wavefront acquired at the wavefront sensor.

8. The method according to claim 7,
   wherein said determining the misalignment of the first system includes reflecting the optical wavefront at the first alignment hologram contained in a first component of the first system, and wherein said redirecting the second optical wavefront includes transmitting the optical wavefront though one of
   a) the first measurement hologram contained in a second component of the first system, said first and second components of the first system being spatially distinct from one another; and
   b) the first measurement hologram contained in the first component of the first system.

9. The method according to claim 7, wherein said determining the error includes at least one of
   i) reflecting the second optical wavefront at a surface of the optical workpiece; and
   ii) transmitting the second optical wavefront through the optical workpiece twice.

10. The method according to claim 9, comprising reflecting light from the second optical wavefront at a reference reflector separated from the first system by the optical workpiece.

11. The method according to claim 7, further comprising:
   partially reflecting the optical wavefront at the first alignment hologram of the first system towards the wavefront sensor to form a reflected wavefront,
   at least reducing the misalignment of the first system by minimizing a figure of merit determined based on a measurement of a phase of the reflected wavefront at the wavefront sensor; and
   spatially fixating a component of the first system with respect to the axis after said figured of merit has been minimized.

12. The method according to claim 7, wherein said aligning the second system includes reducing each of spatial tilt, azimuthal angular deviation, transverse shift, and longitudinal shift of the at least one alignment reference component by measuring said error of the reflected first optical wavefront, that has transmitted through the second alignment hologram, with wavefront sensor.

13. A method for measuring an optical wavefront characterizing an optical workpiece, the method comprising:
   determining a misalignment of a first system with respect an axis with the use of an optical wavefront incident thereon from a wavefront sensor,
      wherein the first system contains at least a first alignment hologram, a first measurement hologram, and a second alignment hologram;
   redirecting first and second optical wavefronts, formed by transmitting the optical wavefront respectively through the first and second alignment holograms, towards a second system containing a mounting substrate and an alignment reference component disposed in a first opening of the mounting substrate;
   forming reflected first and second optical wavefronts by respectively interacting the first and second optical wavefronts with the optical workpiece fixedly positioned in a second opening of the mounting substrate and the alignment reference component;
   propagating the reflected first and second optical wavefronts through the first system towards the wavefront sensor;
   spatially aligning the alignment reference component affixed at the mounting substrate to eliminate at least one of spatial tilt, azimuthal angular deviation, transverse shift, and longitudinal shift of the alignment reference component with respect to the axis by changing at least one of position and orientation of the mounting substrate with respect to the axis based on a measurement of light from the reflected second optical wavefront acquired at the wavefront sensor; and
   determining an error in the reflected first optical wavefront based on a measurement of light from the first reflected optical wavefront acquired at the wavefront sensor.

14. The method according to claim 13, comprising substantially nullifying the misalignment of the first system by:
   partially reflecting the optical wavefront at the first alignment hologram of the first system towards the wavefront sensor to form a reflected wavefront,
   at least reducing the misalignment of the first system by minimizing a figure of merit determined based on a measurement of a phase of the reflected wavefront at the wavefront sensor; and
   spatially fixating a component of the first system with respect to the axis after said figure of merit has been minimized.

15. The method according to claim 14, wherein said determining the error in the reflected first optical wavefront is carried out after of at least reducing the misalignment of the first system has been accomplished.

16. The method according to claim 14, wherein, when the wavefront sensor is an optical interferometer, at least one of the following conditions is satisfied:
   a) said determining the error in the reflected first optical wavefront includes determining a difference between a spatial profile of the reflected first optical wavefront that has transmitted through the first system towards the optical interferometer and a spatial profile of a reference optical wavefront generated internally to the interferometer;
   b) said spatially aligning the alignment reference component includes forming alignment optical interference fringes by optically interfering, at an output of the optical interferometer, the reflected second optical wavefront that has transmitted through the first system and the reference optical wavefront; and
   c) said at least reducing the misalignment includes reorienting the component of the first system to substantially eliminate at least one of the spatial tilt, azimuthal angular deviation, transverse shift, and longitudinal shift of said component with respect to the axis based on transformation of the optical interference fringes formed at the output of the optical interferometer.

17. The method according to claim 13, wherein the first system includes first and second components that are spatially-distinct and separable from one another, wherein the first component contains one or more of the first alignment hologram, the second alignment hologram, and the first measurement hologram while the second component contains remaining of the first alignment hologram, the second alignment hologram, and the first measurement hologram.

18. The method according to claim 13, wherein each of said redirecting and spatially aligning is carried out without a relative movement between the workpiece and the mounting substrate and without a relative movement between the alignment reference component and the mounting substrate.

19. The method according to claim 13, wherein said redirecting the second optical wavefront by interacting said second optical wavefront with the alignment reference component includes at least one of
   a) reflecting said second optical wavefront by a reflective hologram contained in the second optical system;

b) reflecting said second optical wavefront at a reference surface of an optical element holder held in a respectively-corresponding opening of the mounting substrate; and c) reflecting said second optical wavefront at a reference surface of an optical element mounted in the optical element holder held in the respectively-corresponding opening of the mounting substrate.

20. The method according to claim 13, wherein the redirecting first and second optical wavefronts includes:
redirecting a plurality of measurement optical wavefronts, each formed by transmitting the optical wavefront through a plurality of the measurement holograms of the first system, and
forming simultaneously a plurality of reflected measurement optical wavefronts by respectively interacting each of the plurality of measurement optical wavefronts with a corresponding workpiece from a plurality of workpieces disposed in respectively-corresponding openings in the mounting substrate.

21. An apparatus for measuring an optical wavefront representing an optical workpiece, the apparatus having an axis and comprising:
a wavefront sensor;
a first repositionable system containing a first alignment hologram, a first measurement hologram, and a second alignment hologram and disposed across the axis
to form a primary alignment wavefront by reflecting a first portion of light output from an optical wavefront delivered from the wavefront sensor and incident onto the first repositionable optical system, and
to transmit a second portion of said light output;
a second repositionable system containing
an alignment reference component and
at least one optical workpiece held in a fixed position and a fixed orientation with respect to the alignment reference component,
wherein the second repositionable system is disposed to reflect, respectively, a first optical wavefront from the second portion and a second optical wavefront from the second portion through the first repositionable system towards the wavefront sensor;
and
a positioner configured to simultaneously change at least one of a position and an orientation of the alignment reference component and at least one of a position and an orientation of the at least one optical workpiece.

22. The apparatus according to claim 21, comprising a mounting substrate installed across the axis and separated from the wavefront sensor by the first repositionable system,
and wherein at least one of the following conditions is satisfied:
a) the alignment reference component includes at least one of a reflective hologram attached to the mounting substrate, a reference surface of an optical element holder attached to the mounting substrate, and a reference surface of an optical element in the optical element holder attached to the mounting substrate;
b) the at least one optical workpiece is affixed to the mounting substrate;
c) the at least one optical workpiece includes a plurality of optical workpieces, each held in a fixed position and orientation with respect to the alignment reference component;
d) the at least one optical workpiece and the alignment reference component are removably affixed in the mounting substrate; and
e) the positioner is operably cooperated with the mounting substrate to change the at least one of position and orientation of the alignment reference component and the at least one optical workpiece simultaneously while changing at least one of position and orientation of the mounting substrate.

23. The apparatus according to claim 21,
wherein the at least one optical workpiece is held in an opening defined through a mounting substrate, and
further comprising a reference reflector positioned to receive light from the second wavefront through the at least one optical workpiece and reflect said light back onto itself, through the at least one optical workpiece, the first repositionable system, and into the wavefront sensor.

24. The apparatus according to claim 1, wherein the alignment reference component comprises at least one of a reflective hologram and a reference reflector.

25. The method according to claim 7, wherein the alignment reference component comprises at least one of a reflective hologram and a reference reflector.

* * * * *

UNITED STATES PATENT AND TRADEMARK OFFICE
CERTIFICATE OF CORRECTION

PATENT NO. : 12,053,240 B2
APPLICATION NO. : 17/323231
DATED : August 6, 2024
INVENTOR(S) : James Burge and Chunyu Zhao It is certified that error appears in the above-identified patent and that said Letters Patent is hereby corrected as shown below:

In the Claims

Column 20, Line 12, "aligment" should read "alignment."

Column 20, Line 42, "aligment" should read "alignment."

Signed and Sealed this
Third Day of September, 2024

Katherine Kelly Vidal
*Director of the United States Patent and Trademark Office*